United States Patent [19]

Csillag et al.

[11] Patent Number: 4,793,706

[45] Date of Patent: Dec. 27, 1988

[54] PROCESS AND EQUIPMENT FOR THE DETERMINATION OF GRAIN SIZE DISTRIBUTION OF PARTICLES IN SUSPENSION

[75] Inventors: Zsolt Csillag; Denes Bulkai; Ferenc Farkas; Ferenc Kovács; Gábor Márton; Mária Fodor, all of Budapest, Hungary

[73] Assignee: Magyar Aluminiumipari Troszi, Budapest, Hungary

[21] Appl. No.: 3,427

[22] PCT Filed: May 30, 1986

[86] PCT No.: PCT/HU86/00035

§ 371 Date: Jan. 9, 1987

§ 102(e) Date: Jan. 9, 1987

[87] PCT Pub. No.: WO86/07147

PCT Pub. Date: Dec. 4, 1986

[30] Foreign Application Priority Data

May 30, 1985 [HU] Hungary .................. 2070/85

[51] Int. Cl.[4] ........................................... G01N 15/02
[52] U.S. Cl. ..................................... 356/335; 250/564; 356/427
[58] Field of Search ................ 356/335, 426, 427; 250/564; 73/61.4

[56] References Cited

U.S. PATENT DOCUMENTS

| 2,379,158 | 6/1945 | Kalischer | 356/335 X |
| 3,739,180 | 6/1973 | Carlson | 356/335 X |
| 3,879,129 | 4/1975 | Inoue | 356/335 |
| 4,159,639 | 4/1979 | Simms et al. | 73/61.4 X |
| 4,282,745 | 8/1981 | Burr | 73/61.4 |

FOREIGN PATENT DOCUMENTS 1112770 5/1968 United Kingdom ............. 356/335

Primary Examiner—Davis L. Willis
Assistant Examiner—Matthew W. Koren
Attorney, Agent, or Firm—Schweitzer & Cornman

[57] ABSTRACT

A system and an associated process are described for the determination of grain size distribution of particles in suspension. The suspension is settled in a settling tank and optical density measurements of the suspension are taken and from this the grain size distribution is determined. According to the invention, the suspension is homogenized by circulating it in the settling tank, then circulating is stopped and the optical density is repeatedly measured in the settling tank on at least three points with deviating spacings. The equipment described is a settling tank (1) for the suspension, a device for the measurement of optical density in the settling tank (1) and a computing unit calculating the grain size distribution from the optical density values measured. The settling tank (1) is equipped with a means for the circulation of the suspension and there are at least three measuring heads (2,3,4,5,6) along the settling tank (1) sensing the optical density.

16 Claims, 5 Drawing Sheets

PROCESS AND EQUIPMENT FOR THE DETERMINATION OF GRAIN SIZE DISTRIBUTION OF PARTICLES IN SUSPENSION

BACKGROUND OF THE INVENTION

This invention relates to both the is a process and equipment for the determination of grain size distribution of particles in suspension.

The known or prior art and equipment processes for the determination of grain size distribution are characterized by the fact that the measurement is carried out by drawing samples independent of the technological process under laboratory conditions. The time required for measurement and evaluation is fairly long therefore this kind of solution is not suitable for continuous measurement and process control. The equipment called "Analysette 20" of the Fritsch-make represents the basis of a process for the determination of grain size distribution wherein the settling rate/velocity of particles is determined by photoextinction density measurement and further on the grain size distribution as a function of the path of settling. By this instrument the samples taken from the technological process are similarly treated under laboratory conditions. The principal part of the unit is a cell filled with suspension sample which is, after some predetermined time, scanned by a photoextinction measuring head moved continuously in an opposite direction to the settling. As a result of movement of the measuring head the extinction of the smaller particles can be determined after a shorter path of settling and the measurement can be performed within 15–20 minutes i.e. far before total settling would be completed. Disadvantage of the solution lies in the condition that measurement cannot earlier be terminated and evaluated before measuring a moving head reaches the surface of liquor, at the same time the accuracy of measurement improves in direct proportion to the height of the column of liquid which means that higher accuracy is associated with longer measuring time. Minimum measuring time with this kind of measurement of result resulting in acceptable results would take about 15 minutes. This time is too long to apply the solution for direct control of the technological processes.

A further disadvantage of the known device lies in the condition that the measuring range of grain size distribution is comparatively small because measuring time can only be reduced by the reduction of useful height of the cell thus limiting the upper limit of measuring range and the interfering effect on the photoextinction measurement of the reflection of liquor surface in the cell limits the lower limit of measuring range. Particles exhibiting a settling path less than 1 cm can no longer be measured by this device, it only provides acceptable measuring results in the particle range of 1–200 $\mu$m.

SUMMARY OF THE INVENTION

For a number of technological processes, e.g. classification, sizing, grinding, crystallization, settling and agglomeration, a solution for the measurement of grain size distribution is needed. The results of which should be useful directly for the contemporary regulation and control of the process. The invention is based on the recognition that for the determination of the photoextinction grain size distribution, the optical density is repeatedly measured at several points in the container holding the suspension, and the grain size distribution is determined from the data obtained by the use of a digital data processing unit. This way, partly the measuring range can be extended, partly the measuring time can be reduced thus the measuring results may directly be used for the control of some technological processes.

Accordingly the invention represents a process for the determination of grain size distribution of particles in suspension in the course of which the suspension is allowed to settle in a settling tank while the optical density of the suspension in the settling tank is measured and from this the grain size distribution is determined.

According to the invention, the suspension is homogenized by circulating it in the settling tank, then circulating is stopped and optical density is repeatedly measured at at least three points of different height. Repeating of measurements should expediently be made at 0.0001–1 second interwals for 30–300 seconds.

When applying more, preferably five measuring heads along the settling tank, a settling tank of an appropriate height can partly be used resulting in the extension of the upper measuring limit, partly the fast processing of results obtained at given time intervals by the measuring heads by a microprocessor or microcomputer decreases measuring time considerably. It is of advantage in practice that measurement by the measuring heads is made very quickly by the use of change-over-switch for measuring points according to the given intervals one by one, rather than all at once. In order to optimize the optical density measurement, a standard solution is added to the suspension such as to obtain an optical density of 0.5–1.0, preferably, 0.7–0.9 of the mixture. For standard solution an aqueous or organic solvent solution of the dispersing reagent is expediently to be added. Accuracy of measurement may be increased if the temperature of suspension, respectively the mixture and standard solution is kept at constant value, preferably at temperatures exceeding by 2°–10° that of the ambient one.

The measurement can be made more accurate if prior to circulating the suspension, plain standard solution is circulated first in the settling tank and the optical density of standard solution and the dark current of the measuring device is measured. By storing the values thus obtained the optical density values measured for the suspension can be corrected.

It is of advantage during the process according to the invention to measure, at the beginning of measurement yet during circulation, the initial optical density corresponding to the maximum masking at all places, then to form their reciprocals and multiply the latter by the least value of initial optical density. Optical density values measured afterwards could be corrected by the corrected values thus obtained. Optical density data measured during settling are stored in the corrected state. Based on the point of time of successive measurements for every measuring head the corresponding grain size is determined. The grain size ranges of the neighbouring measuring heads become overlapped, and making use of this, in the course of preprocessing the measurement data starting from the lowermost measuring head only those points will be accepted to be valid which relate to coarser grains than the uppermost measuring head could have detected. This way, one particular grain size corresponds to but a single optical density. This reduction of data, according to the invention, not only reduces the data pairs to be transmitted to get further processed to their fifth part, but assures the selection of data pertaining to the longest measured path thus being most accurate. In the course of preprocessing, the mass proportions are calculated from the data pairs in a way that the product of the individual grain size and optical density data pairs is divided by the sum of those products. The mass proportions determine already the cumulative grain size distribution.

The invention also includes a system for the determination of grain size distribution of particles in a suspension. The equipment used in the novel system comprises a settling tank for the suspension, a device for measuring the optical density of the suspension in the settling tank and a computing unit for the determination of grain size distribution from the optical density values measured. According to the invention, the settling tank in the equipment is equipped with a circulating system for the suspension, and at least three measuring heads to sense the optical density are arranged at heights of different spacings along the settling tank.

It is advantageous to provide the settling tank preferably of tubular shape with an overflow rim on its upper end and a lid with its inner surface not reflecting inwards. The lid prevents the upper level in the settling tank from reflecting and thus interferring. This way, the uppermost measuring head can directly be arranged below the lid and thus the lower limit of measurement can substantially be reduced. It is advantageous to arrange the measuring heads at increasing spacings, for instance in the way that the uppermost measuring head is located under the lid at a distance of 0.01–0.00H, the second one below the first one at a distance of 0.1–0.03H and the other measuring heads one by one at still increasing distances, where H represents the height of the settling tank.

In one operative embodiment the circulating system comprises a circulating tank, a first pipe coming from the former leading to the bottom part of the settling tank, a circulating pump built-in in the first pipe and a second pipe carrying the suspension leaving the upper part of the settling tank and recycling the substance into the circulating tank. If the circulating tank is equipped with a temperature controlling device, so constant temperature of the suspension in the settling tank can be assured.

It is of advantage if the equipment according to the invention is provided with a tank holding the standard solution the former being connected by pipe with the circulating tank. A controllable valve is built in this pipe. The standard solution is partly used for calibration before measurement partly for the dilution of the suspension to be measured. In order to increase accuracy the thermal regulation of the standard solution tank is also advantageous.

The settling tank, the circulating tank and the standard solution tank are connected on top by a pressure equalizing pipe. The equipment according to the invention is suitable for both laboratory measurements and measurements necessary for controlling a technological process. In the latter case, the circulating tank is linked up over a controllable valve with the pipeline of the suspension of the technological process to be tested. It is expedient to install a charging pump between the circulating tank and the pipeline of the technological process in order to alternatively feed suspension from the pipeline or standard solution from the standard solution tank into the circulating tank. By this method the required mixing ratio can be adjusted. For flushing the equipment according to the invention after measurement the circulating tank is connected over a controllable valve with the pipe of flushing liquor. The circulating pipe, on its lower section is connected to a drain pipe over a controllable valve. A liquor sensor is provided in the drain pipe indicating the condition for the processing and control unit that drainage has been completed.

With the equipment according to the invention such kind of realization is practicable where all the measuring heads, pumps and controllable valves are connected to a single processing and control unit, the latter comprising also a digital data processor. This processing and control unit carries out the control of the entire measuring unit and the preprocessing of optical density data supplied by the measuring heads. It is expedient to transmit the preprocessed data over a digital bus to an evaluation unit comprising another digital data processor. Thus the processing and control unit is capable during the processing time of transmitted data of controlling the subsequent measuring cycle. The invention is further explained with reference to the drawings representing the practicable realization modes, where

BRIEF DESCRIPTION OF THE INVENTION

FIG. 1 shows a block diagram of the various pieces of equipment according to the invention, FIG. 2 is a schematic representation of the various interconnections of the measuring unit of the system according to the invention, FIG. 3A and 3B is a block diagram of the interconnections of the processing and control units of the equipment according to the invention, FIG. 4 shows the block diagram of the evaluation unit of the equipment according to the invention.

DETAILED DESCRIPTION OF THE PREFERRED EMOBIDENTS

Figure 1:
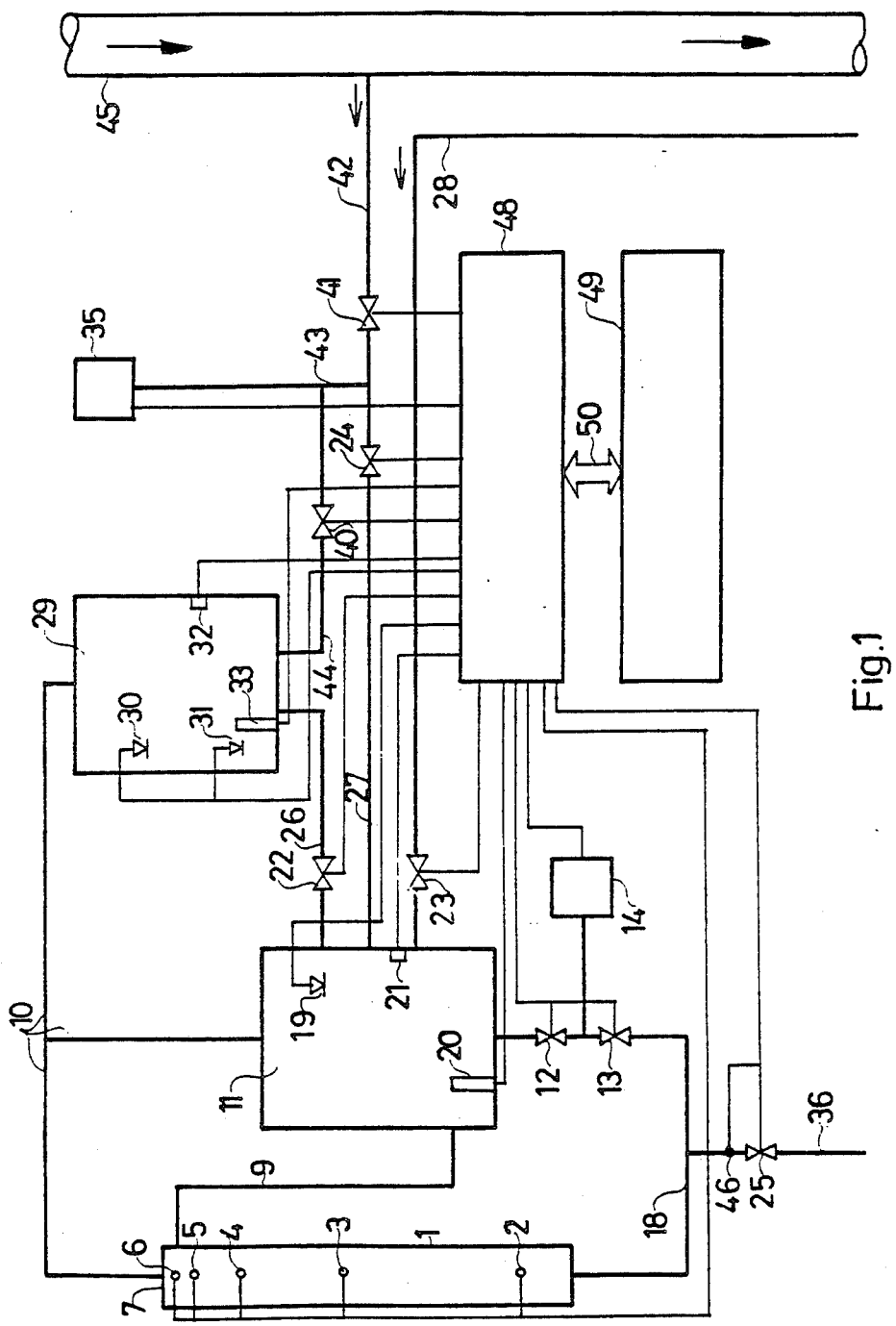

In FIG. 1 measuring heads 2, 3, 4, 5 and 6 are located along settling tank 1. Said heads 2, 3, 4, 5 and 6 are arranged to measure optical density of the liquor and suspension being held in the settling tank 1. The settling tank 1 is, at its lower and upper ends connected to a recycling circulating system comprising a circulating tank 11, a pipe 18 leading from the bottom of the former to the bottom of the settling tank 1, further a return pipe 9 leading from the upper section of the settling tank 1 to the circulating tank 11 and a circulating pump 14 installed in the pipe 18 between valves 12 and 13. The pipe 18 is connected at its lower track to the pipe 36 over a controllable valve 25. To indicate the completion of drainage the pipe 36 is fitted with a liquor sensor 46. To provide temperature control for the circulating tank 11 a heating device 20 and a temperature sensor 21 is provided. To indicate the filled-up state a level detector 19 is fitted in the circulating tank 11. The circulating tank 11 is connected over a controllable valve 22 and by a pipe 26 with a standard solution tank 29 which for heat control is similarly fitted with a heating device 33, and a temperature sensor 32, moreover, for the indication of filled-up state with level detectors 30 and 31. Pipe 45, carrying the suspension to be measured, is connected to circulating tank 29 by means of controllable valves 24 and 41 and by pipe 42. The pipe 45 is one pertaining to those of the technology or industrial process being measured, respectively, it may run parallel thereto. The circulating tank 11 is connected with a pipe 28 to carry the flushing liquor, e.g. water over a controllable valve 23. The standard solution tank 29 is connected with a pipe 43 of a feed pump 35 by a pipe 44 and over a controllable valve 40. The pipe 43 is connected with the pipe track between the controllable valves 24 and 41. This way the feed pump 35 charges either suspension over the pipe 42 into the circulating tank 11 with the valve 40 closed, or standard solution into the same with the valve 41 closed. During charging material by the pump 35 the valves 24 and 41, respectively, valves 24 and 41 should alternately be operated. The settling tank 1, circulating tank 11 and the standard solution tank 29 are interconnected on their upper part by a pressure equalizing pipe 10.

Control of measuring heads 2, 3, 4, 5 and 6 respectively, reception of their measured data as well as the control of valves 12, 13, 22, 23, 24, 25 and 40 and 41 further of pumps 14 and 35 is performed by a data processing and control unit 48. The processing and control unit 48 is further linked up with the heating devices 20 and 33 used for the temperature control of the circulating tank 11 and the standard solution tank 29, and the temperature sensors 21 and 32 as well. Similarly, the processing and control unit 48 receives the signals of level detectors 19, 30 and 31. The processed data are transmitted by the processing and control unit 48 via a bus 50 to an evaluation unit 49.

Figure 2:
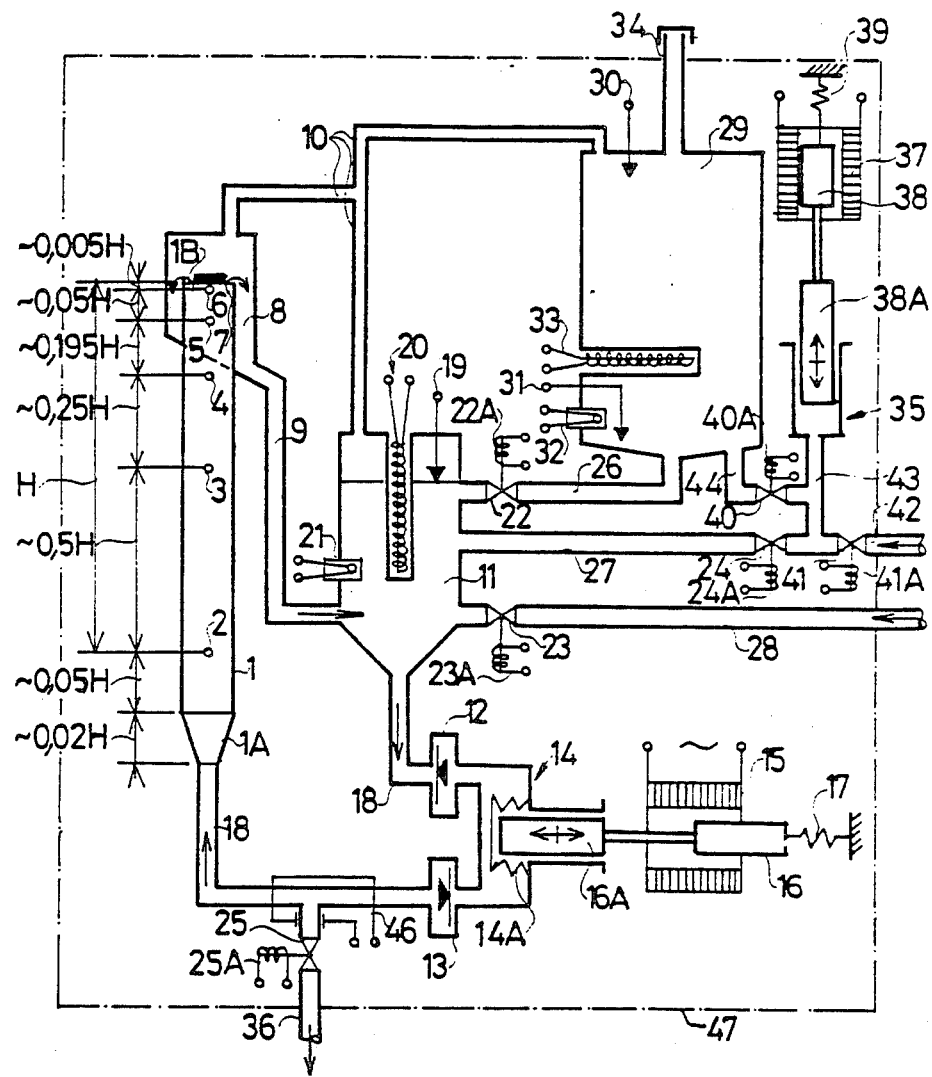

An advantageous and more detailed realization mode of measuring unit 47 of the equipment according to FIG. 1 is shown in FIG. 2. In FIG. 2 the settling tank 1 is a vertical tube having a bottom inlet portion in the shape of a frustum of a cone in order to provide uniform flow pattern. At the upper end of settling tank 1, however, the liquor suspension flows over an overflow rim 1B and returns from liquor collecting channel 8 over a pipe 9 into the circulating tank 11. There is a lid 7 on top of the settling tank 1, its inner surface having a mat black finish, e.g. it is made of a rough plate covered with platinum black on its bottom side, in order to avoid the reflection caused by the upper surface of liquor in the settling tank 1 which would interfere with the extinction measurement. This way, the uppermost measuring head 6 can be located quite near to the lid 7, e.g. about 0.005H away from it, where H is approximately the height of the settling tank 1. The distance between the measuring heads 6 and 5, in the example is about 0.05H, that between the measuring heads 5 and 4 is about 0.195H, that between the measuring heads 4 and 3 is about 0.25H and that between the measuring heads 3 and 2 is about 0.5H. The lowermost measuring head 2 is located at a distance of about 0.05H from the bottom of the settling tank 1, however, the height of the inlet part 1A is about 0.02H. In this operative embodiment the value for H comes to about 1 meter. The settling tank 1 is provided with heat insulation in order to avoid heat convection and is located in a lightshielded shaft enabling the extinction measurement. An exemplary realization of the measuring heads 2, 3, 4, 5 and 6 is given in FIG. 3A.

In FIG. 2 the pump 14 is a diaphragm pump equipped with a bellow-shaped diaphragm 14A, a piston 16A and a magnetic core 16 moving together with the former being displaced by an operating coil 15 against a spring 17. The operating coil 15 is supplied with changeable frequencies. On both sides of the pump 14 there are silicon-rubber membrane valves 12 and 13 installed. The valve 12 opens on the suction effect of the pump 14, the valve 13 opens on the delivery action of the same. The feed pump 35 is of the similar design fitted with magnetic core 38, piston 38A, operating coil 37 and spring 38. In this case, however, the operating coil 37 operates the piston 38A by a long stepped impulse. By this operation the valves 24 and 41 are synchronously controlled while the charging of suspension coming over the pipe 42 takes place, respectively the similar happens to valves 24 and 40 if the standard solution coming over the pipe 44 is charged. It can be seen in the figure that all the valves 22, 23, 24, 25, 40 and 41 are electromagnetically operated by the corresponding operating coils 22A, 23A, 24A, 25A, 40A and 41A. For aeration purposes the standard solution tank 29 is provided with a pipe stub leading to the atmosphere. The latter is covered by a cap provided with a filter insert. There is a liquor sensor 46 provided for which is indicating the completion of discharge being for instance an oscillometric measuring condenser due to flammable solution or suspension possibly used.

Figure 3A:
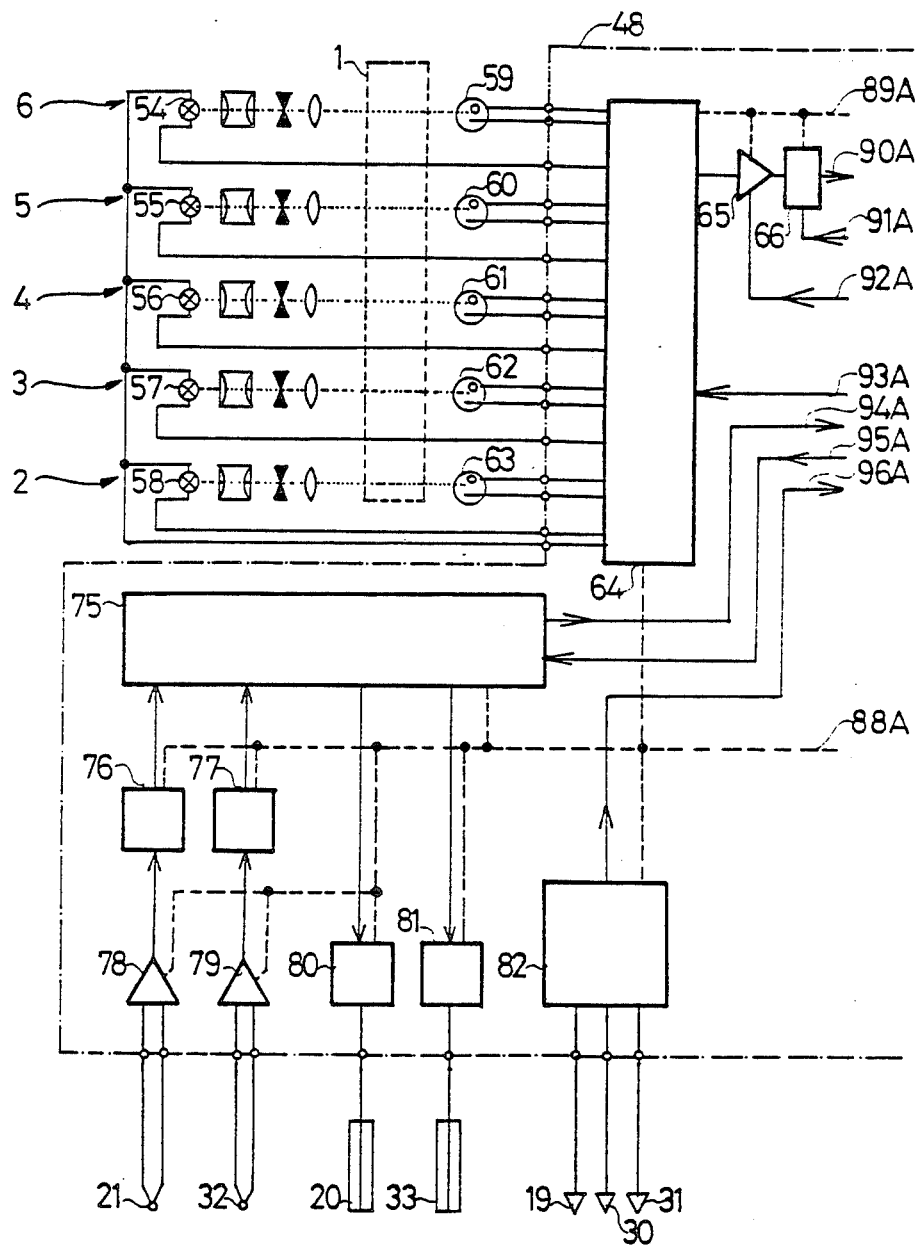
Figure 3B:
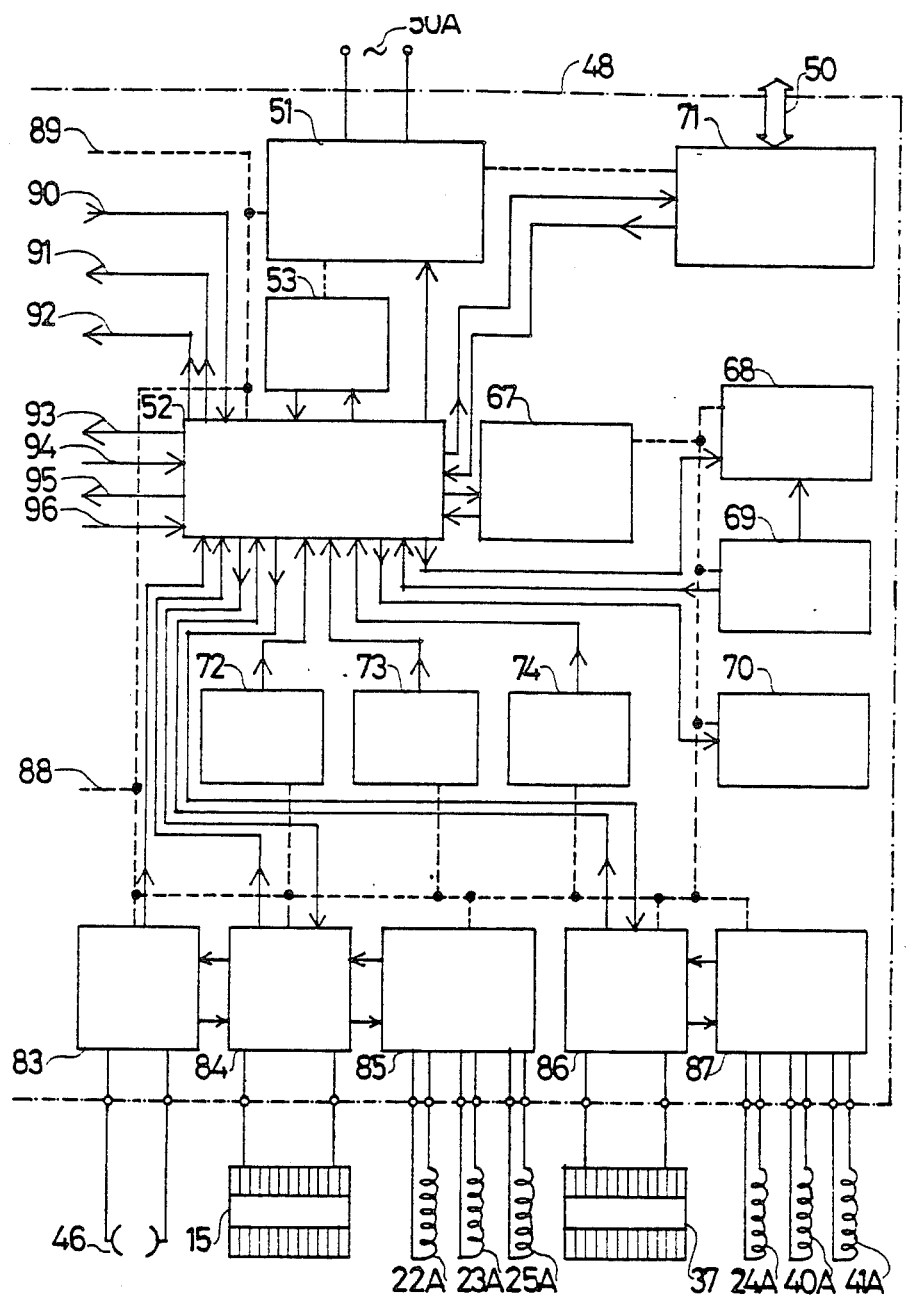

Signal transmitting and control lines leading to the processing and control unit 48 have not been indicated in FIG. 2. Those are shown in FIGS. 3A and 3B representing an operative embodiment of the processing and control unit 48. FIGS. 3A and 3B constitute a single figure where the lines 88, 89, 90, 91, 92, 93, 94, 95 and 96 are connected to the corresponding lines 88A, 89A, 90A, 91A, 92A, 93A, 94A, 95A and 96A.

Power supply for the processing and control unit 48 is provided by the power supply unit 51 assuring a noise-suppressed power fitted with alternating or direct current output terminals.

With all the outputs there is a possibility to report the short or open circuit of interconnected functional units and to give an alarm signal. The identity number of defective unit is indicated by the photodiode. The power supply voltage output lines are drawn in dashed lines. The central unit of the processing and control unit 48 is a microprocessor 52. It performs all the control functions and carries out the preprocessing of optical density data measured. It transmits the preprocessed data via an interface unit 71 to the bus 50 which is connected with the evaluation unit 49. The microprocessor 52 is connected with a clock generator 53 providing timer signals continuously for logging, as well as it separately indicates the measuring time and checks the lapse of maximum time of measurement set. By setting the maximum time of measurement on a keyboard 69 the operator actually determines the minimum particle diameter to be measured (e.g. for 1-2 minutes 1 $\mu$m, for 2-5 minutes already less than 1 $\mu$m).

There are further units attached to the microprocessor 52: a keyboard 69, a display 68, a printer 70, a Random Access Memory or RAM memory 67, as well as Read Only Memory or ROM memories 72, 73 and 74. This as a whole represents substantially a data processing device. The display 70 is used for the visualization of questions, conditions of measurement and data measured. Its purpose is partly the use of the equipment also as a laboratory instrument, partly to enable the operator conducting the measurement for an industrial process to directly intervene on the spot and check up the consequence or result of the intervention, respectively. The keyboard 69 is required for the input of material parameters and denomination of the standard solution and for the operation on the site, respectively. These input values, answers, orders/instructions are also stored in the RAM memory 67. The ROM memory 72 holds the control program of calibrating measurement carried out before the measurement. The ROM memory 73 holds the evaluation and preprocessing programs of the measurement, whereas the ROM memory 74 holds the main program controlling the measuring process.

Further units attached to the microprocessor 52 are an electronic circuit 82 of the level detectors 19, 30 and 31, electronic circuit 83 of the liquid sensor 46, a pump control unit 84 driving the operating coil 15 and a pump control unit 86 driving the operating coil 37. Substantially, the pump control unit 84 is a frequency controller. The required frequency depending on the maximum grain size is calculated by the microprocessor 52 based on the measuring main program stored in the ROM memory 74. The pump control unit 84 controls also the valve control unit 85 driving the operating coils 22A, 23A and 25A corresponding to the order received from the microprocessor 52. The pump control unit 86 controls also the valve control unit 87 driving the operating coils 24A, 40A and 41A corresponding to the order received from the microprocessor 52. Temperature control of the circulating tank 11 and the standard solution tank 29 is performed by the temperature control unit 75 which is on starting from the moment of applying power to the equipment irrespective of the operation of the microprocessor 52. The temperature control unit 75 comprises two independent temperature control subunits. To one of them are attached the temperature sensor 21 through an amplifier 78 and an analogue-digital converter 76, as well as the heating device 20 through a switching relay 80. To the other subunit the temperature sensor 32 is connected via an amplifier 79 and an analogue-digital converter 77, as well as the heating device 33 through a switching relay 81. The measuring heads 2, 3, 4, 5 and 6 are also connected with the microprocessor 52. The measuring head 2 comprises a photodiode 58, the pertaining optics (condenser and diaphragm), as well as a photosensor 63, e.g. photo resistor or photoelement. Similarly, the measuring heads 3, 4, 5, 6 comprise photodiodes 57, 56, 55 and 54 and corresponding photosensors 62, 61, 60 and 59, respectively. The measuring heads 2, 3, 4, 5 and 6 are successively operated by the microprocessor by the help of a measuring point selector 64. The measuring point selector 64 applies current successively on the photodiodes 58, 57, 56, 55 and 54 and in the meantime it switches the outputs of photosensors 63, 62, 61, 60 and 59 to the input terminal of a gain-controlled amplifier 65 the output terminal of which is connected via an analogue-digital converter 66 with the microprocessor 52. Eitehr the amplifier 65 of the analogue-digital converter forms logarithmic values out of measured values. This way the measured extinction values are transmitted in the digital form to the microprocessor 52 which stores them in the RAM memory.

The system according to the invention operates as follows:

Before the measurement of optical density of the suspension, a preliminary measurement is performed according to the control program stored in the ROM memory. In the course of the latter reference measurement is made with the measurement heads 2, 3, 4, 5 and 6. Therefore, by opening the valve 22 the circulating tank 11 and the settling tank 1 is filled up with standard solution while the pump 14 is running. When filling with plain standard solution is completed and indicated by the level detector 19 for all the measuring heads 2, 3, 4, 5 and 6 the values $D=0$ and $D=\infty$, better to say the optical density of the standard solution and the dark current of the measuring head are measured.

Subsequently, to the standard solution in the circulated system samples are given in small batches from the suspension to be analyzed by the use of feed pump 35 as long as the optical density of the mixture of standard solution and the suspension to be analyzed reaches $D=0.7-1$. During circulation the mixture of standard solution and suspension is homogenized. In favour of this the velocity of circulation should be such that even the largest particle does not start settling.

In the course of circulation the starting $D_{O1} \ldots D_{On}$ optical density, where n represents the number of measuring heads, corresponding to maximum masking of the adjusted mixture of liquor is measured for all the measuring heads. The microprocessor 52 forms reciprocal values of the latter and multiplies the reciprocal values with the least measured starting $D_{Oi}$ optical value ($D_{Oi}/D_{O1} \ldots D_{Oi}/D_{Oi} \ldots D_{Oi}/D_{On}$). It stores the correction factors less than unit or even the unit thus obtained and subsequently corrects the optical density values going to be measured for every measuring head after subtracting the stored dark current value by the foregoing factors eliminating hereby the differences resulting from the deviating characteristic curves of the measuring heads.

When starting measurement, the circulation is halted and settling of particles can take place which can be carried out in the settling tank by the measuring heads 2, 3, 4, 5, and 6 at nearly same point of time, expediently at intervals ranging 0.002-0.2 s, expediently for a period of 90-120 s by means of photoextinction measurement. Full measuring time will be set in the function of settling rate/velocity of the particle least in size yet to be measured. The microprocessor 52 stores the optical density values measured during settling in a corrected form in the RAM memory. Based on the points of time of successive measurements, as well as the prevailing conditions of temperature, density, viscosity, the microprocessor 52 computes for every individual measuring head the least and largest measurable grain size (equivalent grain diameter). The grain size ranges thus resulted overlap each other. The microprocessor 52 selects from the optical density values corresponding to the individual measuring times i.e. particle diameters that one which pertains to the longest path of measurement. To this, starting from the lowermost measuring head, it accepts only those optical density values to be valid which relate to coarser grains than the measuring head arranged above the one before was able to measure. In such an assembly of data thus reduced, one grain size corresponds only to a single optical density value. On making the product of grain size and the pertaining optical density value the microprocessor 52 computes the relative weights, their sum and the mass proportions by forming the quotient of relative weights and the sum. The data pairs of grain size - mass proportion determine the cumulative grain size distribution, thus they may be listed or the distribution may be drawn on the printer 70 and/or the data pairs may be transmitted over the bus 50 to the evaluation unit 49.

After having measured the optical density values, the circulating system is drained by opening the valve 25 and is cleaned with flushing liquor by opening the valve 23.

Then the filling-up with the subsequent suspension sample can be started immediately by the feed pump 35.

Figure 4:
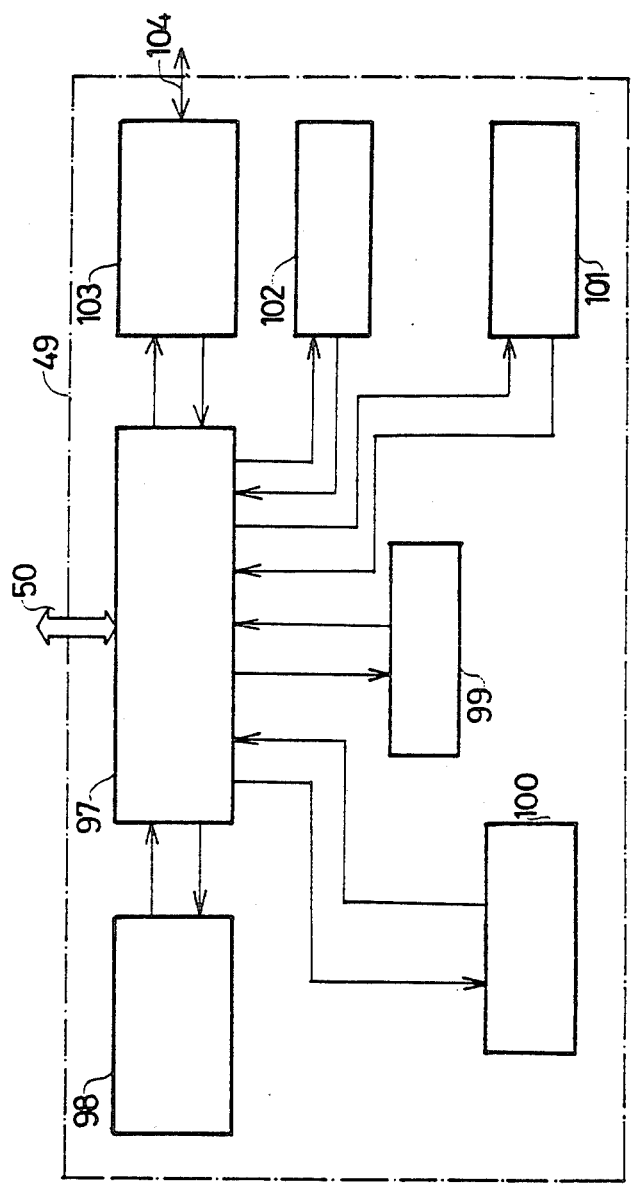

The evaluation unit 49 shown in FIG. 4 comprises a digital data processing device 97 which is either a microcomputer carrying out detailed processing of measured data or an object-oriented microprocessor-furnished process controlling small computer, moreover, it comprises a display 98 for the visualization of data and promoting the communication (in case of microcomputer it can be a constituent of it), further a keyboard 99 for data input and communication (this also forms a constituent of the microcomputer), an interface unit 103 for a high capacity central process control computer, the connection being performed by the data bus 104, a programme store 102 which is for instance a floppy-disc store for storing users' own specific programs, data logger 101 which is a floppy-disc unit for the quick storage of measured data rendering possible the separation of measurement and data processing and the shifting in time (e.g. if checking takes place hourly at 10 points then it is about 30 minutes, so for further processing another half an hour is at disposal) and finally the ROM memory with read only programs forming a part of the measuring system which the user cannot change. The program store 102, however, renders possible that the user can extend the area of application by programs of his own.

The subroutines of the ROM memory 100 render possible the performance of the following tasks for the evaluation unit 49:

(1) The measuring data pretreating and reducing subroutine reads the mass proportion and grain size data pairs by records (e.g. by tens), approaches them by a third-degree parabolic arc, then counts down from this at integral $\mu$-meters ($\mu$) with available path spacings the mass proportions (thus again reducing the number of data to its fourth-fifth part). In order to achieve break-free curve fitting it takes two calculated points from the end of the previous stage with multiple weight into consideration. It traces the distribution values thus obtained, further on the differential and integral (cumulative) curves, too and lists out the same. These data will be the basis of further calculations, Of course, The corresponding heading is also constructed.

(2) Based on the data having been reduced twice in number, the measuring system subroutine carries out the regression of the functions being known by themselves, i.e. Rosin-Rammler (Benet), Schuman-Gaudin, Fauss and Kolmogorov. It prints the point of time of measurements, denomination of samples, denomination of functions, lists out the values of constants, the remarkable distribution values, the mode, the minimum and maximum grain size, the 20% and 80% grain size (36.8% for RR) and an optional minimum and maximum competent grain size (e.g. on selecting $\Delta=5\%$, the 5% and 95% grain size). It lists out the integral (cumulative) and differential distribution function values which it plots by solid lines, indicating besides also the measuring points to demonstrate the merit of approach, moreover, it prints out scattering value or correlation coefficient valid for the entire function. In the case of parallel measurements it also computes the scattering in the function of grain size. It visualizes all data on the display and also on the printer.

(3) Another subroutine computes the regression of a new multi-mode distribution function which is a modified Cauchy distribution. Its advantage lies in the condition that it possesses also an axial section both for minimum and maximum grain size enabling the accurate calculation of the specific surface and other parameters, moreover, it renders also possible the description of asymmetrical distributions and multi-mode distributions by means of superimposition. Its latter feature makes it suitable for the description of processes comprising a classifier, respectively for the solution of fine control of such kind of processes. The machine performs the printing activity outlined with the subroutine (2), however, it does it also by part-density functions and with the integer function, too.

(4) A short subroutine which selects the minimum from the scattering values and prints on basis of this the name of type function providing the best approach, possibly those also being suitable based on the supposition that the scattering does not exceed a certain value.

(5) Evaluation of standard sieve analysis used for checking the values measured by the instrument or for converting the distribution from the equivalent spherical diameters into the actual dimensions. Operation of the subroutine is based on the condition that the progress in time of sieving on siebes of given mesh is well known for the type of material to be measured. This may be carried out by a previous set of tests. As a result of tests a series of data pairs consisting of time and sieve residue is obtained. From these data the most probable sieve residue figures of a perfect sieving can be calculated, serving as a basis of comparison on which the subroutines (2), (3) and (4) could be performed. In the case of grain function considered to be most suitable it forms the quotient of mass proportions obtained with the equipment in question and those with a measure identic with the sieve. In the case of proper measurement the figures will be close to each other. By plotting the latter and carrying out the regression a straight line parallel with the abscissa intersecting the ordinate is obtained the section being the shape factor looked for and valid for the material sample and measuring method given. This latter process could also be applied for other kind of measuring methods. This way the measuring results of various methods could be compared.

(6) Portion of the next subroutine calculates further values calculable from the distributions. It primarily calculates the average grain sizes on basis of various suppositions, e.g. identic specific surface area, equal number of grains, same volume, etc. In addition, it calculates the specific surface area of the sample. In the case of grinding it compares the latter with the value before grinding and calculates the comminution at work and the comminution indices, respectively. If the system measures or receives the quantitative data of flow of the carrying medium, it calculates the concentrations probable from the specific surface area and can thus also supply the estimated mass flows providing basic data required for control.

(7) This subroutine goes on evaluating the (open or closed) grinding circuits. It calculates the comminution efficiency (that with 80%, too), the specific energy consumption, etc. and in the case of a grinding process circuit the cycle factor, too. If previously a series of tests is carried out and the control system is developed for this very task, it will displace the operation of the system towards the minimum energy consumption, e.g. it will set the corresponding material flows, revolution numbers, crushing power, etc.

(8) With the knowledge of distribution of products, the subroutine controlling the operation of the sizer valuates the sharpness of sizing. By the known method of using the Tromp-curves or by a new method, i.e. after having searched for the point of intersection of density functions—grain size of separation—on determining (graphical integral) the areas below the curves, it supplies the mass proportion of defective grains in the individual products. On the basis of Tromp-values and the amount of defective grains, by the help of a previous series of tests, it restores the process by adjusting the material flows (feed), revolution numbers, velocity of air (respectively velocity medium), flight angle, etc. corresponding to the minimum energy consumption and the compliance with the quality specifications set.

(9) The subroutine evaluating the selective grinding is based on a previous series of tests in which the distribution of individual mineral components is determined at the optimum impact or shear velocity. The resultant of those is a multimode distribution curve. On determining the partial density functions from the plant-crushed product their deviation from the original experimental data are observed. For instance, the flattening of individual partial density functions indicates the excess of the optimum impact velocity, that is, the velocity/number of revolution/ has to be reduced. After sizing the distribution of these partial density functions in the coarse, respectively fine product should be checked and the sizer controlled (conforming with the subroutine (3) in a way that the individual partial density functions appear as far as possible merely in one of the products.

(10) At the end of the process a mixture having proper chemical and grain size composition has to be formed of the products of grinding and sizing procedures. This task is performed by a subroutine operating on the basis of known mathematical processes.

(11) The last subroutine does not—except one—comprise independent parts, merely the modifications of the previous subroutines. Namely, in the area of ore dressing any calculation may be performed by the use of the previous multi-mode distribution function and by the help of the previous subroutines, respectively, only the variables have to be renamed and certain boundary conditions be altered, the latter will be carried out by the partical programs. This package has but a single more independent part which makes the equalizing balances of the concentration basic curves. On carrying out several tests from a certain material the metal respectively component balances will not coincide with all the tests, though there would be need for it, they cannot be directly compared with each other. Therefore, by the help of basic principles of the equalizing calculation and weighting of the measured data the balances are corrected in a way that every balance of partial test can be traced back to the starting material and thus they become suitable for comparison.

For the process according to the invention the following examples of application are given:

EXAMPLE 1

Optical density has been measured in the precipitation system of an alumina plant operating at the temperature range 50°–80° C. exhibiting a grain size distribution range 5–160 μm. The test has been carried out in a settling tank by the use of five measuring heads at a temperature of 60° C. after having optical density adjusted to within D=0.8–0.9 at 0.02 s time intervals for a period of 90 s. On basis of this the grain size distribution has been determined for the control of the precipitation process. The measuring process was very fast and resulted in quick evaluation. This rendered possible to process the samples drawn from the three phases (seed hydrate, product hydrate and an intermediate phase) of the process alternatively in a single measuring equipment. It was aimed to measure and/or control the process and in the function of the result the precipitation technology could be controlled.

EXAMPLE 2

The micronized pigment material sample drawn from the centrifugal sizer/classifier has been measured in a suspension of optical density ranging D=0.8–0.9 in the measuring range 1–50 μm in a settling tank fitted with five measuring heads. The photoextinction measurement has been carried out with the five measuring heads nearly contemporarily at time intervals of 0.02 s, for a period of time of 90 s. The measurement and evaluation took 2 minutes altogether, thus the sizing process could be directly controlled on basis of the measurement.

We claim:

1. Process for the determination of grain size distribution of a suspension of grains in a liquor, where suspended grains of less than 1 micron in size are made to settle in a settling tank using optical signals obtained during the settling of the suspension in the settling tank, comprising the steps of:

circulating the suspension through the settling tank to form a homogeneous distribution of suspended grains therethrough;

terminating the circulation;

measuring the optical density of the suspension, repeatedly in situ, with a plurality of light detection means positioned in at least three fixed, increasingly spaced-apart places along the length of the settling tank, opposite an equal plurality of similarly spaced-apart light sources; and determining, from the optical density measurements obtained, the most probable size of the grains in suspension by means of equalizing calculations.

2. Process according to claim 1, comprising the further steps of:

measuring the optical density at at least three places at time intervals ranging from about 0.001 to about 1.0 seconds; and repeating the measurements for a period of time ranging from about 30 to about 300 seconds.

3. Process according to claim 2, comprising the further steps of:

adding a standard solution of as dispersing agent to the suspension during circulation, to adjust the optical density to a value of between 0.5 to 1.0.

4. Process according to claim 3, comprising the further step of:

regulating the temperature of the suspension in the settling tank (1) not to exceed ambient temperature by more than 2°–10° C.

5. Process according to claim 4, comprising the further steps of:
   initially circulating a plain standard solution through the settling tank (1), prior to circulating the suspension of grains to be measured; and
   measuring the the optical density of the standard solution and the dark current of each measuring device, in at least three places in the settling tank (1), to determine an initial optical density corresponding to a value of maximum masking for each measuring device.

6. Process according claim 5, wherein the step of determining the initial optical density corresponding to the maximum masking, comprises the steps of:
   forming the reciprocal value of the optical density;
   multiplying the reciprocal values so formed by the least initial optical density value measured to obtain correction factors; and
   correcting the subsequently measured optical density values the suspended grains by the correction factors thus obtained.

7. A system for the determination of grain size distribution of grains suspended in a liquid suspension, the system comprising:
   a settling tank (1) for holding the grains in suspension;
   the settling tank (1) having:
      (a) means for circulating the suspension therethrough; and;
      (b) a plurality of at least three measuring heads (2, 3, 4, 5, 6) for measuring the optical density of the suspension, at various positions in the settling tank, spaced from each other;
   optical means for measuring the optical density of the suspension in the settling tank;
   a computer processing unit;
   means applying the measured optical density as an input to the computer processing unit;
   the computer processing uunit determining the grain size distribution from the measured optical density values;
   an overflow rim (1B) fitted about the upper end of settling tank (1); and
   a lid (7) having an inner non-reflecting surface fitted at the upper end of settling tank (1).

8. The system of claim 7, further comprising:
   a plurality of at least five measuring heads (2, 3, 4, 5, 6) arranged the length of the settling tank (1);
   the uppermost, first measuring head (6), is positioned under the lid (7), at a distance of 0.03 to 0.003H therefrom;
   the second, next lower, measuring head (5) is positioned at a distance of about 0.1–0.03H from the first measuring head (6); and
   the remaining measuring heads (4, 3, 2) are positioned at increasing distances from each next adjacent head;
   where H represents the height of the settling tank (1).

9. The system of claim 8, wherein the means for circulating the liquid suspension comprises:
   a circulating tank (11);
   a first pipe (18) connecting the lowest portion of the circulating tank (11) to the lowest portion of the settling tank (11);
   a circulating pump (14) in the first pipe (18); and
   a second pipe (9) through which the liquid suspension from the upper part of the settling tank (1) is returned to the circulating tank (11).

10. The system of claim 9, further comprising:
    a first heat regulating device (20) for maintaining the temperature of the liquid in the circulating tank (11) at a predetermined level;
    a standard solution tank (29), connected to the circulating tank (11) by a third pipe (26) and;
    a remotely controllable first valve (22), in the third pipe (26), for regulating the flow of standard solution therethrough.

11. The system of claim 10, further comprising:
    a second heat-regulating device (33) in the standard solution tank (29) for maintaining the temperature of the standard solution in the tank (29) at a predetermined, given level.

12. The system of claim 11, further comprising:
    a fourth pipe (10) connected to the settling tank (1), to the circulating tank (11) and to the standard solution tank (29) for maintaining equal ambient pressures in the tanks (1, 11 and 29);
    a fifth pipe (27,42) connected between the pipe (45) carrying the suspension to be tested and the circulating tank (11); and
    a second controllable valve (24,41) in the fifth pipe (27,42) for controlling the flow of the suspension to be tested into the circulating tank (11).

13. The system of claim 12, further comprising:
    a feed pump (35), between the circulating tank (11) and pipe (45), to selectively feed into circulating tank (11), through the fifth pipe (42,27), either;
    the suspension to be tested, flowing in pipe (45), or;
    standard solution, from the standard solution tank (29).

14. The system of claim 13, further comprising:
    a sixth pipe (28), for providing liquor to flush the circulating tank (11);
    a third valve (23), for controlling the flow of liquor to flush the circulating tank (11);
    a seventh pipe (36), connected to the first pipe (18), for draining liquor from both the circulating tank (11) and the settling tank (1);
    a control valve (25), in the seventh pipe (36), to control the flow of liquid suspension or liquor draining from the tanks (1 and 11); and
    a fluid sensor (46), in the seventh pipe (36), for detecting the presence of any liquid suspension or liquor in the seventh pipe (36).

15. The system of claim 14, further comprising:
    a processing and control unit (48); and
    a digital data processor;
    the digital data processor having as inputs thereto data from the measuring heads (2, 3, 4, 5, 6), and outputs therefrom applied as inputs to control the operation of the pumps (14,35) and the processing and control unit (48).

16. The system of claim 15, wherein the digital data processor further comprises:
    a digital data bus (50), and
    an evaluation unit (49);
    the digital data bus (50) connecting the processing and control unit (48) to the evaluation unit (49).

* * * * *